United States Patent [19]

Howe

[11] 3,964,300
[45] June 22, 1976

[54] SKI GAUGE

[76] Inventor: John G. Howe, Jamestown Star Route, Boulder, Colo. 80301

[22] Filed: Mar. 17, 1975

[21] Appl. No.: 558,696

[52] U.S. Cl. ................................................ 73/100
[51] Int. Cl.² ......................................... G01N 3/20
[58] Field of Search ............................. 73/100, 161

[56] References Cited
UNITED STATES PATENTS

| 3,646,810 | 3/1972 | Taysom et al. .................. 73/100 X |
| 3,889,518 | 6/1975 | Denouter et al. ........... 73/432 SD X |

Primary Examiner—Jerry W. Myracle
Attorney, Agent, or Firm—Cushman, Darby & Cushman

[57] ABSTRACT

The "bending stiffness" and camber of a ski are combined in a single integrated measurement by clamping the ski at its central portion to another surface and positioning a non-deflecting measuring device between the ski and the surface at a selected location intermediate the ski end and said central portion.

4 Claims, 3 Drawing Figures

SKI GAUGE

BACKGROUND OF THE INVENTION

The present invention involves the measurement of skis and more particularly, the determination of what is generally called "ski stiffness". This parameter is a principal one in establishing the ski's performance characteristics.

The structural components and dimensions of a ski construction control what is known as its "bending stiffness". However, a ski also is formed with camber which affects the deflection of the ski. Thus, in order to measure what a skier is primarily interested in--the ski's overall deflection characteristics--an integrated measurement of bending stiffness and camber is required. Such a measurement is perhaps best called the determination of deflection stiffness, and throughout the following description that term will be utilized instead of ski stiffness.

It is believed that heretofore no device has been developed to permit a simple accurate determination of deflection stiffness. However, the present invention provides a means for integrating bending stiffness and camber so as to obtain a meaningful measurement of this parameter.

SUMMARY OF THE INVENTION

Briefly, the invention comprises a non-deflecting type of measurement device, such as a hydraulic gauge, which is selectively positioned between the running surface of a ski being measured and another surface while the ski is clamped intermediate its ends to said surface. The measurement device deflects the ski a given distance causing the gauge to develop a reading reflecting the combined "bending stiffness" and initial camber of the ski.

DETAILS OF THE INVENTION

A preferred embodiment of the invention just outlined will be described with reference to the accompanying drawings wherein.

Figure 1:
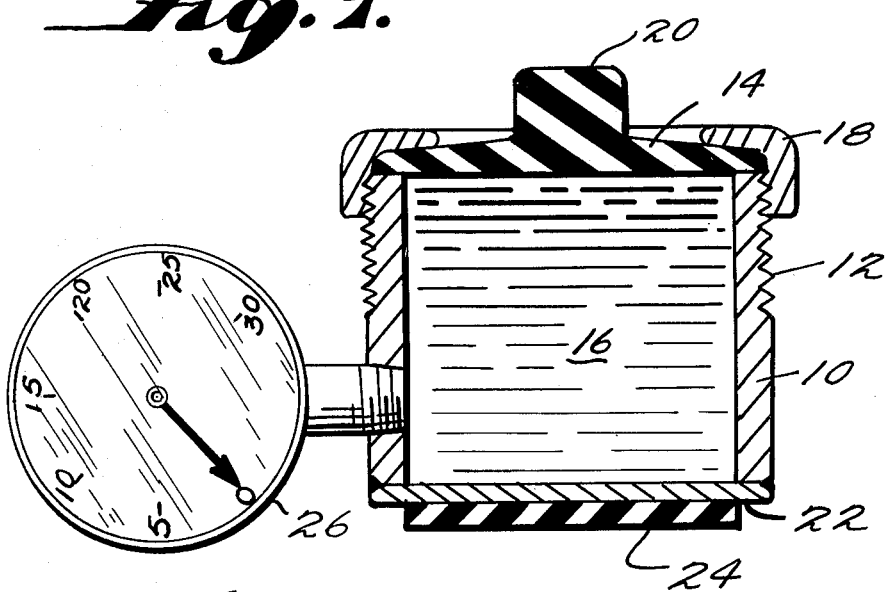
FIG. 1 is a cross-sectional view of a hydraulic gauge suitable for use as a measurement device.

Referring to FIG. 1, the hydraulic gauge illustrated comprises a cylindrical body 10 provided with threads 12 at one end thereof. A flexible diaphragm 14 capable of transmitting force to a fluid within cylinder 10 such as oil 16, covers one end of the cylinder. The diaphragm is held in place by a threaded ring 18 which engages threads 12 on the cylinder. The ring 18 is conformed to permit a projecting portion 20 of diaphragm 14 to extend above the level of the ring in order to engage a running surface of the ski being tested. The opposite end of cylinder 10 is sealed by an end plate 22 which preferably has a protective rubber coverning 24 at its underside. A conventional pressure gauge 26 is mounted on the side of cylinder 10. Any pressure developed in the fluid 16 as a result of force being applied to diaphram 14 results in a reading being developed on gauge 26.

The measuring device just described is of the non-deflecting type. That is, the application of force on diaphragm 14 does not substantially alter the diaphragm's position. While the hydraulic device shown in FIG. 1 is the preferred form of a non-deflecting unit, it will be appreciated that other essentially non-deflecting force gauges could be used. For example, a strain gauge of the electrical transducer type also may be utilized.

Figure 2:
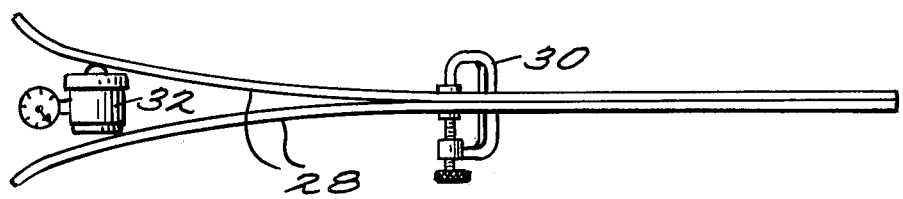
FIG. 2 is an illustration of the measurement of deflection stiffness of the forebodies of a pair of skis.
Figure 3:
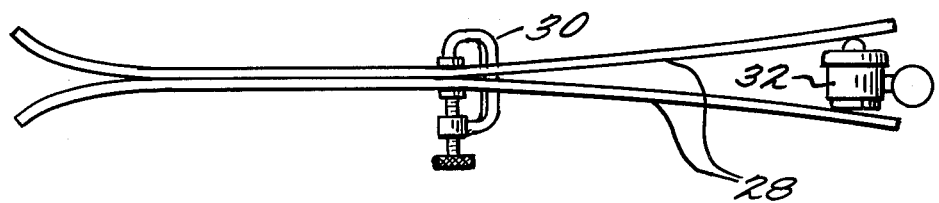
FIG. 3 is an illustration of the measurement of deflection stiffness of the afterbodies of a pair of skis.

The procedure employed in measuring deflection stiffness is illustrated in FIGS. 2 and 3. FIG. 2 relates to measurements taken at the forebodies of the skis, while FIG. 3 shows the arrangement utilized in measuring deflection stiffness at the afterbodies. In each case, a pair of skis 28 is clamped together by a conventional C-clamp 30 at a preselected location in the central portion of the skis where they are cambered. The gauge could also be used if the skis are held together at the central location by hand. The measuring device described with respect to FIG. 1 then is inserted between the running surfaces of the clamped skis. This device is designated as 32 in FIGS. 2 and 3 and is positioned at a predetermined distance from the tips or tails, respectively, of the skis. This predetermined distance is constant for a given length ski in order to yield comparative results between various skis. The unit 32 separates the skis by a distance corresponding to the dimension of the unit, and consequently, the skis are deflected with respect to the point where they are clamped together. In effect, this deflection corresponds to that of a cantilevered beam. The resultant force which is exerted by the skis on the measuring unit 32 is a function of the stresses caused by elimination of the initial, static camber by claim 30 and the bending of the skis a predetermined amount by unit 32. Thus, the measurement recorded by the gauge of unit 32 is an integrated function of the skis' camber and bending stiffness. By following the foregoing procedure for different pairs of skis, comparative results can be obtained.

While the measurement procedure just described employs a pair of skis, it will be apparent that the method also is appropriate to measure the deflection stiffness of a single ski. This is accomplished by clamping the ski to a planar reference surface rather than to a mating ski. The unit 32 then is positioned between the planar surface and the running surface of the ski being measured at a preselected distance from the end of the ski.

What is claimed is:

1. A method for measuring the deflection stiffness of a ski, comprising:
    clamping a running surface of said ski against an additional surface at a central portion of said ski; and
    positioning a substantially non-deflective measuring device between said surfaces at a selected location intermediate said central portion and an end of the ski, said device being responsive to force exerted thereon by said ski to provide an indication of said deflective stiffness.

2. A method as set forth in claim 1, wherein said additional surface is a central portion of a running surface of another ski.

3. A method as set forth in claim 2 wherein said measuring device comprises a hydraulic gauge having a diaphragm which engages the running surface of one of said skis and which transmits force exerted by the engaged ski to fluid within said guage.

4. A method as set forth in Claim 1, wherein said measuring device comprises a hydraulic gauge having a diaphragm which engages the surface of said ski and which transmits force exerted by said ski to fluid within said gauge.

* * * * *